(12) United States Patent
Feld

(10) Patent No.: US 11,724,076 B2
(45) Date of Patent: Aug. 15, 2023

(54) METHODS AND DEVICES FOR URETHRAL TREATMENT

(71) Applicant: ProArc Medical Ltd., Misgav (IL)

(72) Inventor: Yair Feld, Haifa (IL)

(73) Assignee: ProArc Medical Ltd., Misgav (IL)

( * ) Notice: Subject to any disclaimer, the term of this patent is extended or adjusted under 35 U.S.C. 154(b) by 731 days.

(21) Appl. No.: 16/554,774

(22) Filed: Aug. 29, 2019

(65) Prior Publication Data

US 2019/0381291 A1 Dec. 19, 2019

Related U.S. Application Data

(60) Continuation of application No. 14/967,308, filed on Dec. 13, 2015, now Pat. No. 10,406,333, which is a
(Continued)

(51) Int. Cl.
*A61M 29/00* (2006.01)
*A61M 29/02* (2006.01)
(Continued)

(52) U.S. Cl.
CPC ............ *A61M 29/00* (2013.01); *A61M 25/00* (2013.01); *A61M 29/02* (2013.01);
(Continued)

(58) Field of Classification Search
CPC .. A61F 2/2442–2466; A61F 2002/048; A61M 29/00; A61M 25/00; A61M 29/02
See application file for complete search history.

(56) References Cited

U.S. PATENT DOCUMENTS

| 4,660,560 A | 4/1987 | Klein |
| 5,030,227 A | 7/1991 | Rosenbluth et al. |
| (Continued) | | |

FOREIGN PATENT DOCUMENTS

| EP | 0125352 | 11/1984 |
| EP | 1413262 | 4/2004 |
| (Continued) | | |

OTHER PUBLICATIONS

Non-Final Office Action for U.S. Appl. No. 16/048,481 dated Mar. 11, 2022.
(Continued)

*Primary Examiner* — Thomas McEvoy
(74) *Attorney, Agent, or Firm* — Dorsey & Whitney LLP

(57) ABSTRACT

A dilation device for an intrabody lumen, for example, a urethra partially occluded by an enlarged prostate in the form of a curved element configured to be implanted around the lumen and add resilience to the lumen, and a method for dilating such a lumen by implanting a dilation device around the outside of the lumen with at least part of the dilation device embedded in surrounding, thereby preventing clinically significant compression of the lumen. Also, an implantation device for such a dilation device in the form of a mounting device configured to carry the dilation device; and a releasably attached movable holder, with the mounting device and holder configured to deliver the dilation device though a working channel to a desired position in a lumen, and to implant the dilation device through a wall of the lumen to a position surrounding the lumen.

17 Claims, 11 Drawing Sheets

Related U.S. Application Data division of application No. 13/257,651, filed as application No. PCT/IL2010/000229 on Mar. 21, 2010, now abandoned.

(60) Provisional application No. 61/202,634, filed on Mar. 20, 2009.

(51) Int. Cl.
  *A61M 25/00* (2006.01)
  *A61B 18/18* (2006.01)
  *A61F 2/04* (2013.01)

(52) U.S. Cl.
  CPC ... *A61B 18/1815* (2013.01); *A61B 2018/1861* (2013.01); *A61F 2002/048* (2013.01)

(56) References Cited

U.S. PATENT DOCUMENTS

| | | |
|---|---|---|
| 5,133,713 A | 7/1992 | Huang et al. |
| 5,269,802 A | 12/1993 | Garber |
| 5,643,340 A | 7/1997 | Nunokawa |
| 5,674,242 A | 10/1997 | Phan et al. |
| 5,766,203 A | 6/1998 | Imran et al. |
| 5,921,982 A | 7/1999 | Lesh et al. |
| 6,070,589 A | 6/2000 | Keith et al. |
| 6,319,282 B1 | 11/2001 | Nishi |
| 6,673,101 B1 | 1/2004 | Fitzgerald et al. |
| 7,004,965 B2 | 2/2006 | Gross |
| 7,279,002 B2 | 10/2007 | Shaw et al. |
| 7,632,297 B2 | 12/2009 | Gross |
| 8,016,845 B1 | 9/2011 | Sauer |
| 8,145,321 B2 | 3/2012 | Gross |
| 2002/0007222 A1 | 1/2002 | Desai |
| 2002/0010489 A1 | 1/2002 | Grayzel et al. |
| 2002/0032486 A1 | 3/2002 | Lazarovitz et al. |
| 2002/0032488 A1 | 3/2002 | Brekke et al. |
| 2002/0035391 A1 | 3/2002 | Mikus et al. |
| 2003/0055313 A1 | 3/2003 | Anderson et al. |
| 2003/0060870 A1 | 3/2003 | Reever |
| 2003/0069467 A1 | 4/2003 | Desmond, III et al. |
| 2003/0167088 A1 | 9/2003 | Abraham et al. |
| 2003/0191479 A1 | 10/2003 | Thornton |
| 2003/0216814 A1 | 11/2003 | Siegel et al. |
| 2004/0030217 A1 | 2/2004 | Yeung et al. |
| 2004/0064139 A1 | 4/2004 | Yossepowitch |
| 2004/0181235 A1 | 9/2004 | Daignault et al. |
| 2005/0055087 A1 | 3/2005 | Starksen |
| 2005/0137716 A1 | 6/2005 | Gross |
| 2006/0095058 A1 | 5/2006 | Sivan et al. |
| 2006/0149308 A1 | 7/2006 | Melsheimer et al. |
| 2006/0167540 A1 | 7/2006 | Masters et al. |
| 2006/0173517 A1 | 8/2006 | Gross |
| 2006/0229711 A1 | 10/2006 | Yan et al. |
| 2006/0271151 A1 | 11/2006 | McGarry et al. |
| 2006/0276871 A1 | 12/2006 | Lamson et al. |
| 2007/0093781 A1 | 4/2007 | Kugler et al. |
| 2009/0156977 A1 | 6/2009 | Daignault et al. |
| 2009/0264987 A1 | 10/2009 | Gale |
| 2009/0297582 A1 | 12/2009 | Meyer et al. |
| 2010/0100195 A1 | 4/2010 | Gross |
| 2010/0130815 A1 | 5/2010 | Gross et al. |
| 2010/0137893 A1 | 6/2010 | Kilemnick et al. |
| 2010/0292715 A1 | 11/2010 | Nering et al. |
| 2010/0312054 A1 | 12/2010 | Beyar et al. |
| 2012/0010645 A1 | 1/2012 | Feld |
| 2013/0268086 A1 | 10/2013 | Creedon et al. |
| 2014/0012192 A1 | 1/2014 | Bar-On et al. |
| 2016/0000455 A1 | 1/2016 | Golan et al. |
| 2016/0096009 A1 | 4/2016 | Feld |
| 2018/0344995 A1 | 12/2018 | Bar-On et al. |
| 2019/0381291 A1 | 12/2019 | Feld |

FOREIGN PATENT DOCUMENTS

| | | |
|---|---|---|
| EP | 1415681 | 5/2004 |
| JP | 2004-147812 | 5/2004 |
| WO | WO 94/04081 | 3/1994 |
| WO | WO 01/43664 | 6/2001 |
| WO | WO 2007/048437 | 5/2007 |
| WO | WO 2007/109621 | 9/2007 |
| WO | WO 2008/056194 | 5/2008 |
| WO | WO 2008/142677 | 11/2008 |
| WO | WO 2010/106543 | 9/2010 |
| WO | WO 2012/123950 | 9/2012 |
| WO | WO 2014/141278 | 9/2014 |
| WO | 2021250588 A1 | 12/2021 |

OTHER PUBLICATIONS

U.S. Appl. No. 14/768,766, filed Aug. 19, 2015.
Final Office Action for U.S. Appl. No. 14/768,766 dated Apr. 2, 2021.
Final Office Action for U.S. Appl. No. 14/768,766 dated Aug. 23, 2021.
Non-Final Office Action for U.S. Appl. No. 14/768,766 dated Jul. 22, 2020.
Official Action dated Jul. 22, 2020 from the US Patent and Trademark Office Re. U.S. Appl. No. 14/768,766. (25 pages).
Requisition by the Examiner Dated Apr. 3, 2020 From the Innovation, Science and Economic Development Canada, Canadian Intellectual Property Office Re. Application No. 2,939,823. (13 Pages).
Communication Pursuant to Article 94(3) EPC dated Oct. 28, 2019 From the European Patent Office Re. Application No. 14764625.1. (6 Pages).
Advisory Action Before the Filing of an Appeal Brief dated Dec. 27, 2017 From the US Patent and Trademark Office Re. U.S. Appl. No. 14/005,330. (5 pages).
Advisory Action Before the Filing of An Appeal Brief dated Nov. 30, 2018 From the US Patent and Trademark Office Re. U.S. Appl. No. 13/257,651. (3 pages).
Applicant-Initiated Interview Summary dated Feb. 4, 2019 From the US Patent and Trademark Office Re. U.S. Appl. No. 14/768,766. (4 pages).
Applicant-Initiated Interview Summary dated Oct. 6, 2016 From the US Patent and Trademark Office Re. U.S. Appl. No. 14/005,330.
Applicant-Initiated Interview Summary dated Nov. 9, 2017 From the US Patent and Trademark Office Re. U.S. Appl. No. 14/005,330 (3 pages).
Applicant-Initiated Interview Summary dated Feb. 12, 2019 From the US Patent and Trademark Office Re. U.S. Appl. No. 14/967,308. (4 pages).
Applicant-Initiated Interview Summary dated Mar. 15, 2017 From the US Patent and Trademark Office Re. U.S. Appl. No. 14/005,330. (2 pages).
Applicant-Initiated Interview Summary dated Jan. 16, 2018 From the US Patent and Trademark Office Re. U.S. Appl. No. 13/257,651. (3 pages).
Applicant-Initiated Interview Summary dated Apr. 28, 2016 From the US Patent and Trademark Office Re. U.S. Appl. No. 14/005,330.
Communication Pursuant to Article 94(3) EPC dated Feb. 21, 2017 From the European Patent Office Re. Application No. 10714484.2. (4 Pages).
Communication Pursuant to Article 94(3) EPC dated Mar. 23, 2016 From the European Patent Office Re. Application No. 12716658.5.
Communication Pursuant to Article 94(3) EPC dated Sep. 24, 2014 From the European Patent Office Re. Application No. 12716658.5.
Communication Relating to the Results of the Partial International Search dated Jul. 4, 2012 From the International Searching Authority Re. Application No. PCT/IL2012/050094.
Communication Relating to the Results of the Partial International Search dated Nov. 8, 2010 From the International Searching Authority Re. Application No. PCT/IL2010/000229.
Examiner-Initiated Interview Summary dated Nov. 29, 2016 From the US Patent and Trademark Office Re. U.S. Appl. No. 14/005,330. (5 pages).

(56) References Cited

OTHER PUBLICATIONS

International Preliminary Report on Patentability dated Sep. 24, 2015 From the International Bureau of WIPO Re. Application No. PCT/IL2014/050281.
International Preliminary Report on Patentability dated Sep. 26, 2013 From the International Bureau of WIPO Re. Application No. PCT/IL2012/050094.
International Preliminary Report on Patentability dated Sep. 29, 2011 From the International Bureau of WIPO Re. Application No. PCT/IL2010/000229.
International Search Report and the Written Opinion dated Jul. 3, 2014 From the International Searching Authority Re. Application No. PCT/IL2014/050281.
International Search Report and the Written Opinion dated Sep. 13, 2012 From the International Searching Authority Re. Application No. PCT/IL2012/050094.
International Search Report and the Written Opinion dated Jan. 18, 2011 From the International Searching Authority Re. Application No. PCT/IL2010/000229.
Official Action dated Mar. 1, 2017 From the US Patent and Trademark Office Re. U.S. Appl. No. 14/005,330. (17 pages).
Official Action dated Sep. 8, 2017 From the US Patent and Trademark Office Re. U.S. Appl. No. 13/257,651. (19 pages).
Official Action dated Sep. 9, 2016 From the US Patent and Trademark Office Re. U.S. Appl. No. 13/257,651.
Official Action dated Aug. 12, 2014 From the US Patent and Trademark Office Re. U.S. Appl. No. 13/257,651.
Official Action dated Dec. 13, 2018 From the US Patent and Trademark Office Re. U.S. Appl. No. 14/967,308. (13 pages).
Official Action dated Sep. 15, 2015 From the US Patent and Trademark Office Re. U.S. Appl. No. 13/257,651.
Official Action dated Feb. 16, 2016 From the US Patent and Trademark Office Re. U.S. Appl. No. 14/005,330.
Official Action dated Jul. 16, 2018 From the US Patent and Trademark Office Re. U.S. Appl. No. 13/257,651. (23 pages).
Official Action dated Mar. 16, 2015 From the US Patent and Trademark Office Re. U.S. Appl. No. 13/257,651.
Official Action dated Aug. 18, 2017 From the US Patent and Trademark Office Re. U.S. Appl. No. 14/005,330. (19 pages).
Official Action dated Apr. 19, 2017 From the US Patent and Trademark Office Re. U.S. Appl. No. 13/257,651. (26 pages).
Official Action dated Nov. 19, 2018 From the US Patent and Trademark Office Re. U.S. Appl. No. 14/768,766. (63 pages).
Official Action dated Aug. 24, 2016 From the US Patent and Trademark Office Re. U.S. Appl. No. 14/005,330.
Official Action dated Mar. 24, 2016 From the US Patent and Trademark Office Re. U.S. Appl. No. 13/257,651.
Official Action dated Mar. 28, 2018 From the US Patent and Trademark Office Re. U.S. Appl. No. 14/967,308. (52 pages).
Official Action dated Jul. 29, 2019 From the US Patent and Trademark Office Re. U.S. Appl. No. 14/768,766. (25 pages).
Rectification of Obvious Mistake Under Rule 91.1. Dated Jul. 6, 2010 From the International Searching Authority of the European Patent Office Re. Application No. PCT/IL2010/000229.
Restriction Official Action dated Jul. 14, 2015 From the US Patent and Trademark Office Re. U.S. Appl. No. 14/005,330.
Restriction Official Action dated Apr. 20, 2018 From the US Patent and Trademark Office Re. U.S. Appl. No. 14/768,766. (8 pages).
Restriction Official Action dated Apr. 22, 2014 From the US Patent and Trademark Office Re. U.S. Appl. No. 13/257,651.
Restriction Official Action dated Nov. 30, 2017 From the US Patent and Trademark Office Re. U.S. Appl. No. 14/967,308. (8 pages).
Supplementary European Search Report and the European Search Opinion dated Oct. 28, 2016 From the European Patent Office Re. Application No. 14764625.1.
European Search Report and the European Search Opinion dated Jan. 17, 2020 From the European Patent Office Re. Application No. 18215225.6. (7 Pages).
International Search Report and Written Opinion from International Application No. PCTIB2021055063 dated Aug. 10, 2021.
U.S. Appl. No. 17/533,306, filed Nov. 23, 2021.

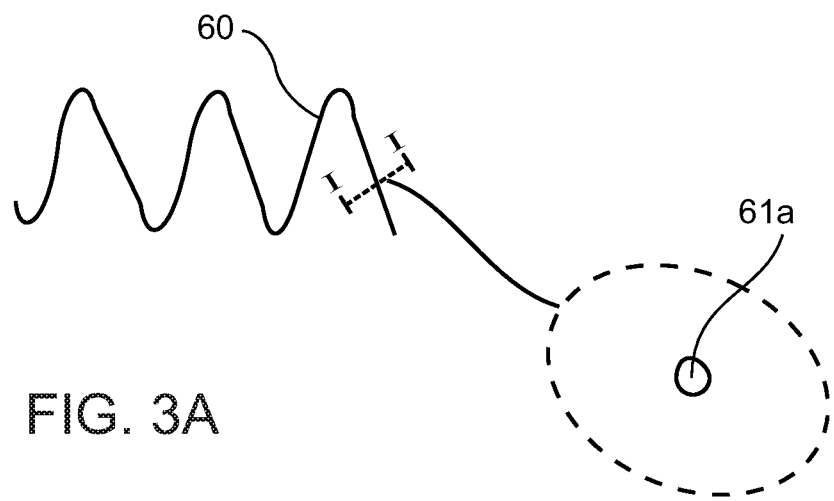
FIG. 3A
FIG. 3B
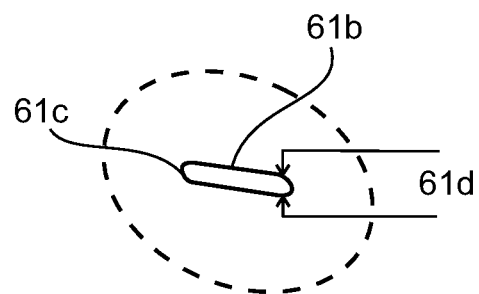
FIG. 3C

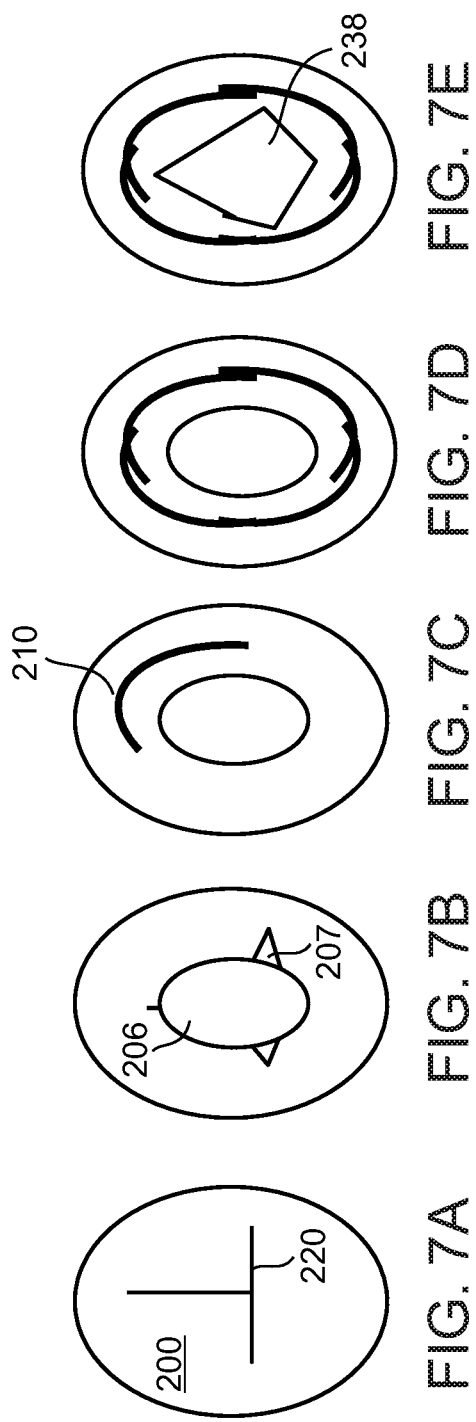

METHODS AND DEVICES FOR URETHRAL TREATMENT

RELATED APPLICATIONS

This application is a continuation of U.S. patent application Ser. No. 14/967,308 filed on Dec. 13, 2015, which is a division of U.S. patent application Ser. No. 13/257,651 filed on Sep. 20, 2011, which is a National Phase of PCT Patent Application No. PCT/IL2010/000229 having International Filing Date of Mar. 21, 2010, which claims the benefit of priority of U.S. Provisional Patent Application No. 61/202,634 filed Mar. 20, 2009. The contents of the above applications are all incorporated by reference as if fully set forth herein in their entirety.

FIELD OF THE INVENTION

The present invention, in some embodiments thereof, relates to methods and devices for treatment of intrabody lumens, and, more particularly, but not exclusively, to methods and devices for dilating and/or assisting in dilation and/or maintaining dilation of the urethra to relieve obstruction resulting, for example from benign prostatic hyperplasia (BPH).

BACKGROUND OF THE INVENTION

It is common for the prostate gland to become enlarged as a man ages. As a male matures, the prostate goes through two main periods of growth, first early in puberty, and then again at around age 25, when the growth begins, and continues on through life. One of the effects of this continued growth can be pressure on the urethra, the passage through which urine passes from the bladder and the penis.

The urethra is surrounded by the prostate for part of its length. Within the confines of the prostate, the urine flows through a passage having a generally triangular cross-section. As the prostate enlarges, the layer of tissue surrounding the prostate restricts the prostate from expanding outward, causing the prostate to constrict the urethral passage. The condition of an enlarged, non-cancerous prostate is called benign prostatic hyperplasia (BPH), or benign prostatic hypertrophy.

Though the prostate continues to grow during most of a man's life, BPH rarely causes symptoms before age 40, but more than half of men in their sixties and as many as 90 percent in their seventies and eighties have some symptoms of BPH. BPH can make it difficult to the bladder to completely empty, and is associated with other urinary system problems well known in the medical field.

Current Treatment

Men who have BPH with symptoms usually need some kind of treatment at some time. Although the need for treatment is not usually urgent, doctors generally advise treatment once the problems become bothersome or present a health risk.

The most commonly used treatments for BPH include drug therapy, minimally invasive mechanical treatment, and surgery.

Among the drugs approved for example, by the U.S. FDA, are Finasteride (Proscar), dutasteride (Avodart), terazosin (Hytrin), doxazosin (Cardura), tamsulosin (Flomax), and alfuzosin (Uroxatral). These drugs act by relaxing the smooth muscle of the prostate and bladder neck to improve urine flow and to reduce bladder outlet obstruction. Use of finasteride and doxazosin together has also been found to be more effective than using either drug.

Drug treatment may only be partially effective in some cases. Researchers have therefore developed a number of mechanical procedures that relieve BPH symptoms but are less invasive than conventional surgery. These include transurethral microwave thermotherapy (TUMT), which uses microwaves to heat and destroy portions of prostate tissue, transurethral needle ablation (TUNA), which employs low-level radio-frequency energy delivered through twin needles to burn away selected regions of the enlarged prostate, and water-induced thermotherapy, which uses heated water to destroy portions of prostate tissue. The use of ultrasound waves to destroy prostate tissue is also undergoing clinical trials in the United States.

Urethral stents have also been employed in some instances, with varying degrees of effectiveness.

Surgical removal of part of the prostate, thereby reducing pressure against the urethra is often regarded as the best long-term solution for patients with BPH. Among the types of surgery commonly employed is transurethral surgery which requires no external incision. Such procedures include transurethral resection of the prostate (TURP), by which prostate tissue is removed, transurethral incision of the prostate (TUIP), by which the urethra is widened by making a few small cuts in the bladder neck where the urethra joins the bladder, and in the prostate gland itself, and laser induced prostate tissue removal.

In the few cases where transurethral surgical procedures are not indicated, open surgery, which requires an external incision, may be used.

SUMMARY OF THE INVENTION

According to an aspect of some embodiments of the invention, a method for dilating a urethra is provided according to which a dilation device is implanted around the outside of a urethra in an area affected by an enlarged prostate with at least part of the dilation device embedded in a surrounding enlarged prostate, thereby preventing clinically significant compression of the urethra.

According to some embodiments, the dilation device is installed transurethrally.

According to some embodiments, the dilation device is implanted by being screwed into the tissue of the prostate.

According to some embodiments, the dilation device is implanted by being pushed into the tissue of the prostate.

According to some embodiments, the dilation device is implanted by being advanced into the tissue of the prostate using an overtube.

According to some embodiments, the dilation device is implanted, and expanded or allowing to expand post-implantation.

According to some embodiments, the dilation device is in the form of a spiral wire.

According to some embodiments, the dilation device is in the form of one or more separate curved sections.

According to some embodiments, the dilation device is formed of a material which expands outwardly around the urethra during and/or after implantation.

According to some embodiments, prior to or during before implantation, the urethra is shaped using an expandable element.

According to some embodiments, the expandable element is not rotated during implantation.

According to some embodiments, the expandable element is a balloon.

According to some embodiments, the length and position of the dilation device is selected not to interfere with an inner bladder valve.

According to some embodiments, the dilation device provides clearance between the enlarged prostate and a lumen of the urethra, and prevents recompression of the urethra due to further enlargement of the prostate.

According to an aspect of some embodiments of the invention, apparatus for implanting a urethral dilation device is provided having a mounting device configured to carry the dilation device, and a releasably attached movable holder, the mounting device and holder being configured to deliver the dilation device though a working channel to a desired position in a urethra, and to implant the dilation device through a wall of the urethra to a position surrounding the urethra.

According to some embodiments, a delivery sheath is provided to receive the dilation device before placement thereof on the mounting device.

According to some embodiments, the delivery sheath is of a shape generally conforming to that of the dilation device.

According to some embodiments, the dilation device is formed of a resilient material, and the mounting device is configured to permit a reduction of a transverse dimension of the dilation device as it passes though the working channel.

According to some embodiments, the implantation apparatus includes a urethral expander.

According to some embodiments, the urethral expander is configured to be rotatably coupled to the holder.

According to some embodiments, the urethral expander is configured to have a known position relative to the holder.

According to some embodiments, the urethral expander is configured to lie to a side of the holder.

According to some embodiments, the urethral expander includes at least one guide channel for the dilation device.

According to some embodiments, the urethral expander is a balloon.

According to an aspect of some embodiments of the invention, a dilation device is provided for a urethra partially occluded by an enlarged prostate having a curved element configured to be implanted around a urethra and add resilience to a urethral lumen.

According to some embodiments, the has a spiral shape.

According to some embodiments, the dilation device is a plurality of curved segments.

According to some embodiments, the dilation device is formed of a resilient material.

According to some embodiments, the dilation device is configured for transurethral implantation.

According to some embodiments, the mounting device and the holder are attached together.

According to some embodiments, the delivery device includes a cage configured to surround the dilation device during implantation.

According to some embodiments, the cage includes an opening allowing the dilation device to exit for implantation.

According to some embodiments, the cage is configured to compress the dilation device and prevent it from expanding while being delivered for implantation.

According to an aspect of some embodiments of the invention, a method is provided for supporting a body lumen, in which a a dilation device is implanted around the outside of the lumen in an area affected by a compression tissue with at least part of the dilation device embedded in a surrounding tissue, thereby preventing clinically significant compression of the lumen.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 3A shows a dilation device in the form of a spiral wire according to some embodiments of the invention, which can be implanted, for example, by the method of FIG. 1;

FIGS. 3B and 3C show exemplary alternative enlarged cross-sections for the wire of FIG. 3A;

FIG. 7A is a fragmentary schematic illustration of an enlarged prostate and a urethra in cross-section helpful in understanding the method of FIG. 6;

FIGS. 7B-7E shows a dilation device in the form of separate curved sections according to some embodiments of the invention, which can be implanted, for example, by the method of FIG. 6, and progression of a method of implantation, for example, the method of FIG. 6;

DESCRIPTION OF SPECIFIC EMBODIMENTS OF THE INVENTION

Figure 1:
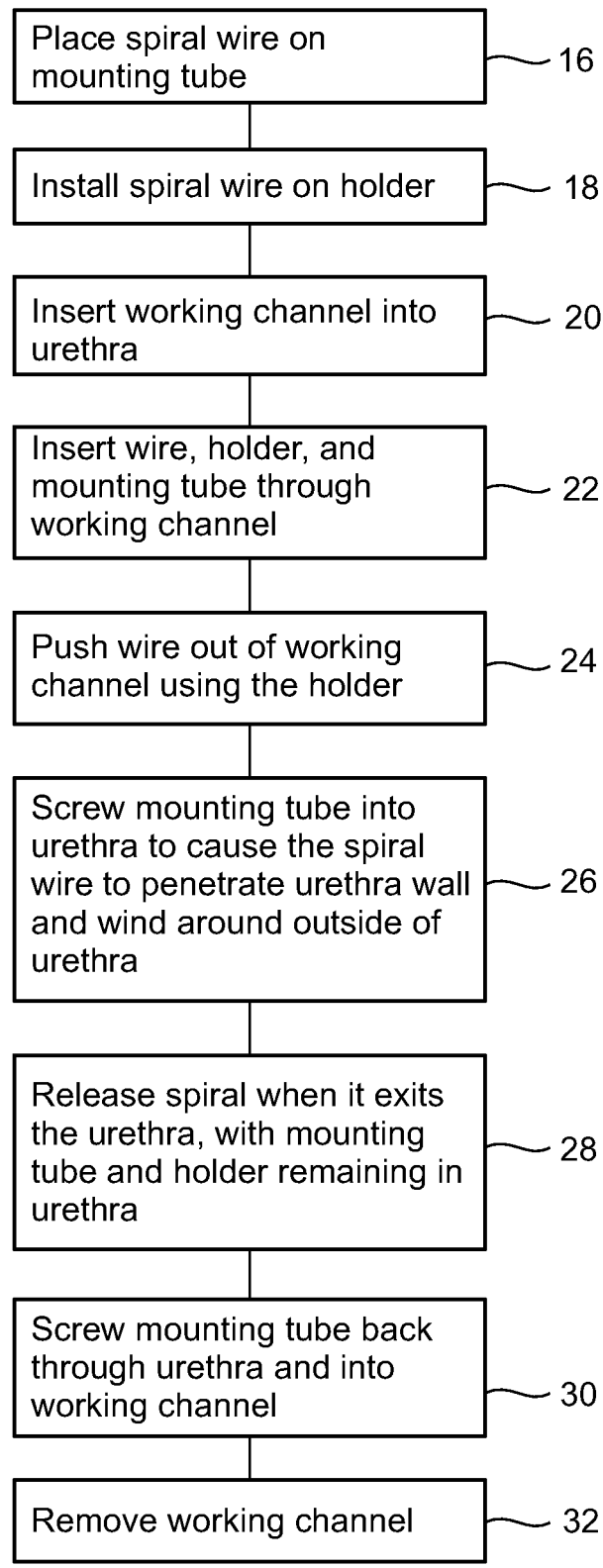
FIG. 1 is a flow diagram illustrating a method of supporting and optionally dilating a generally cylindrical organ, for example, a urethra, to alleviate symptoms of an enlarged prostate relating to urinary flow blockage according to some embodiments of the invention.

The present invention, in some embodiments thereof, relates to methods and/or devices for treatment of intrabody lumens, and, more particularly, but not exclusively, to methods and devices for dilating and/or assisting in dilation and/or maintaining dilation of the urethra to relieve obstruction resulting, for example, from benign prostatic hyperplasia (BPH).

An aspect of some embodiments of the invention relates to treatment of an obstructed urethra, by implanting one or more structural elements in a prostate gland, optionally near a wall of the urethra. Optionally, such structural elements prevent collapsing of the urethra by the pressure of the prostate. A potential benefit of such positioning of structural elements is that urine flow contacts only natural endothelial tissue, onto which it does not aggregate. A potential benefit of such positioning is that endothelial tissue damage is reduced (e.g., to a small number of puncture points), potentially reducing complications and/or restenosis. A potential benefit of such positioning is that pressure damage to the urethral tissue may be reduced. A potential benefit of such positioning is that migration of the structural element may be reduced compared to that of a stent and/or use less invasive anchoring, optionally preventing damage to bladder valves and/or preventing of urine leakage.

According to an aspect of some embodiments of the invention, a dilation device, for example, a curved wire, optionally, an elongated spiral or one or more curved (for example, generally C-shaped arcs), is implanted around the urethra within the confines of the prostate to help treat symptoms of an enlarged prostate, for example, compression of the urethral passage, and to prevent further compression of the urethral passage due to continued enlargement of the prostate. For convenience, the various possible shapes of the dilation device or parts thereof will sometimes be collectively referred to as a "wire".

The wire is optionally made of a biocompatible, for example, metallic material, or of a biodegradable material. Optionally, the wire has a generally rounded or a generally flat cross-section. Optionally, the wire has a widened tip (or tips) and/or edges to prevent piercing damage to the urethra and/or prostate during and after implantation.

Optionally, according to an aspect of some embodiments of the invention, the wire is formed of a resilient or elastic material and/or is configured so that it is able to expand during and/or after implantation, e.g., being formed of a super-elastic or shape-memory material configured to have a desired final shape in the body.

Optionally, in the case of a spiral wire, the length along the urethra is short, for example, 1 cm or less in length, to provide a local dilation, or longer than 1 cm to open longer areas in the urethra. Optionally, several spirals may be implanted along a length of the urethra, e.g., at axially different locations, optionally with some overlap therebetween or with spacing therebetween.

Optionally, one or more separate curved sections may be spaced along the urethra, and/or extend circumferentially around the urethra. Optionally, spirals and separate curved sections may be used together. Optionally, multiple separate curved sections may be installed sequentially or simultaneously, for example, with multiple such sections encircling the urethra. In some embodiments, the urethra is not completely encircled by such implantations.

According to an aspect of some embodiments of the invention, the wire is provided with a drug coating, for example, sirolimus or paclitaxel, etc., which is eluted over time, for example, to treat the prostate (e.g., cause shrinkage or reduce growth) and/or to prevent restenosis. Optionally, the wire may be made of or coated with a radioactive material, or formed of a material capable of being heated by RF energy, for example, by microwaves.

According to an aspect of some embodiments of the invention, the wire is implanted using a delivery device inserted into a urethra through a working channel provided, for example, by a cystoscope, or a catheter, also inserted in the urethra. Optionally, the implantation process is guided visually through the working channel, or in other ways, for example, by ultrasound.

According to an aspect of some embodiments of the invention, the urethra is shaped before implantation, for example using an expanding balloon. Optionally or alternatively, the balloon is used to guide insertion of the device. Optionally, the balloon is maintained in place and includes a guide to guide insertion of the device. In an alternative embodiment, the balloon is maintained in place while a device delivery system is rotated.

In an exemplary embodiment of the invention, one of three insertion methods are used: pushing the wire through the urethral wall into the prostate, screwing the wire around the urethra after a first insertion into the prostate, and inserting the wire covered with an overtube or other delivery system and/or stiffener into the prostate and then retracting the over tube. Other implantation methods may be used as well. In some embodiments, a plurality of wires is inserted simultaneously, for example, at same or different axial locations along the urethra.

In an exemplary embodiment of the invention, the wire is loaded in a delivery system in a linear configuration. A plurality of wires may be loaded simultaneously, for example, for sequential and/or parallel implantation. In other embodiments, the wire is loaded in a non-linear configuration, for example, as a helix or folded. Such a helix configuration may also be used for arc-section devices.

Optionally, the delivery device includes a first part on which the wire is mounted and a second part which is coupled with the first part which is used to move the wire to a desired location for implantation.

Optionally, according to an aspect of some embodiments of the invention, a wire in the form of a spiral is inside a part of the delivery device which surrounds the wire. Optionally, the surrounding part is a sheath that fits closely around the wire, or is in the form of a cage surrounding the outside of the wire in its entirely for delivery to a desired implantation site. The cage optionally prevents expansion of a wire which has been compressed during delivery.

According to an aspect of some embodiments of the invention, the wire is implanted outside the urethra by screwing it to the tissue of the prostate surrounding the urethra. Optionally, for a wire delivered inside a sheath, the wire is implanted by screwing the sheath itself into the tissue of the prostate, and a pusher device is provided to expel the wire from the sheath, and hold the wire in place while the sheath is unscrewed and withdrawn through the working channel.

In some cases, the sheath can be removed by pulling back. For example, where the sheath is soft and serves to reduce friction between the wire and prostate tissue, the sheath may be pulled back.

According to an aspect of some embodiments of the invention, when the delivery device includes an inflatable balloon for expanding the urethra before implantation as mentioned above, the balloon is positioned axially before inflation, or at the circumference of the urethra. Optionally, the balloon includes one or more guide pockets or channels (e.g., on its surface or in its body) through which the wire is passed during implantation. Optionally, the wire is guided during delivery and implantation by a holder separate from the balloon.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways. For example, some embodiments are intended for dilation of other generally cylindrical body cavities such as a bile duct in case of pancreatic or other carcinomas, intestine, e.g. colon carcinoma, blood vessels, or esophagus. In an exemplary embodiment of the invention, in such applications, the length, diameter of coil (e.g., to match tissue lumen) and/or mechanical properties of the wire are adjusted according to the application. Optionally, in some body lumens, implantation is within a wall of the lumen. In other embodiments, implantation is outside the wall of the lumen, for example, in surrounding tissue.

Turning first to FIG. 1, there is shown a flow chart for practice of a method for dilating a urethra according to some embodiments of the invention. This will be discussed in the context of the schematic illustration of a urethra and a surrounding prostate in FIG. 2, a urethra dilation device in the form of a spiral wire illustrated in FIGS. 3A-3C, and an exemplary delivery device illustrated in FIGS. 3D-3F. These will be discussed in detail below.

Figure 2:
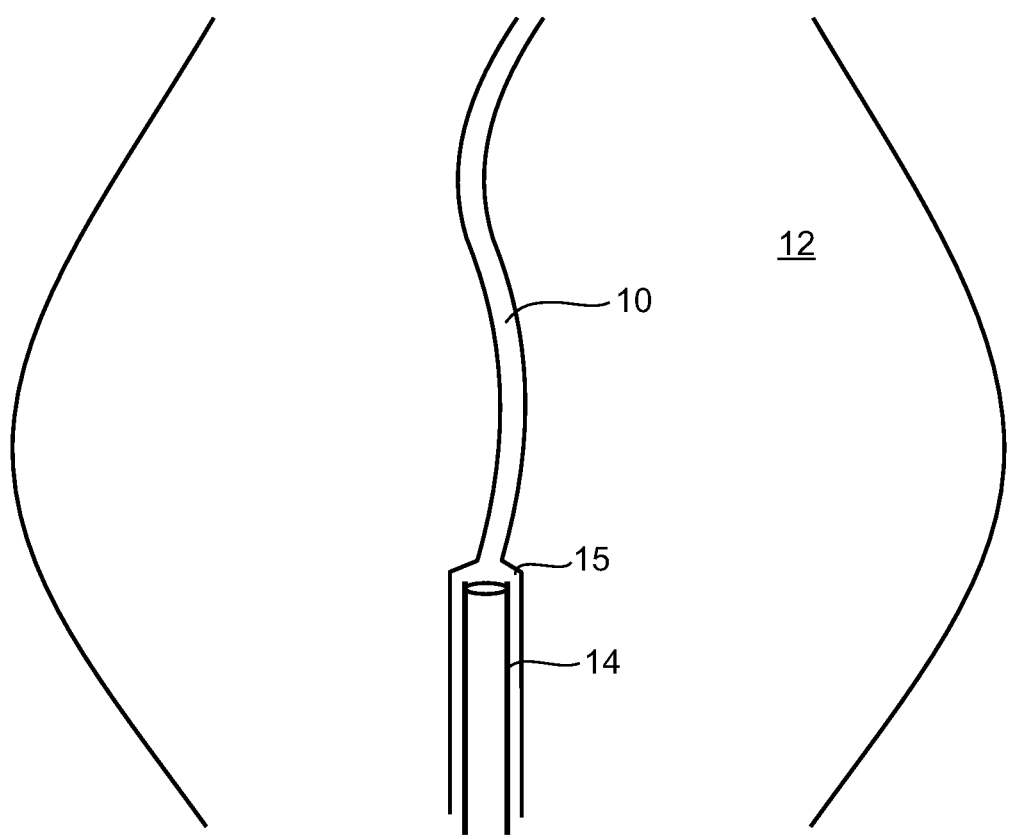
FIG. 2 is a fragmentary schematic illustration of an enlarged prostate and urethra, helpful in understanding the method of FIG. 1.

For reference purposes, in FIG. 2, a urethra 10 is shown compressed by an enlarged prostate 12. Also shown is a working channel 14, for example, of a cystoscope or a catheter, which enlarges the urethra at 15 and provides a pathway for insertion of a delivery device or wire.

With specific reference to FIG. 1, at 16, a dilation device in the form of a spiral wire is placed on a mounting tube. As noted above, such a device may have other functions in addition to or instead of dilation. Optionally, it is placed at the proximal end of the mounting tube, i.e., toward the physician. At 18, the proximal end of the spiral wire is attached to a holder which, in turn, is connected to the mounting tube. At 20, a working channel is inserted into the urethra. Alternatively, the working channel may be inserted in the urethra initially and the wire loaded thereafter. In some embodiments, a very long wire is used, which is snipped after a desired length is inserted. A snipping tool (not shown) may be provided at the distal end of the working channel, optionally as a closable sharp annulus, or as a separate inserted tool.

At 22 and 24, the wire, the holder and the mounting tube are passed through the working channel to a desired location for implantation. In an exemplary embodiment of the invention, the location is selected so that the wire will support the urethra along the entre length of the prostate, possibly with some proximal extension. Optionally or alternatively, the location (and/or length of wire) is selected so that the bladder neck will not be damaged. Optionally or alternatively, the location is selected so that operation on the inner bladder valve is not interfered with. Optionally or alternatively, at least some wire is inserted near the inner valve, possibly resisting over-compression thereof by an enlarged prostate.

At 26 and 28, when the distal end of the wire is out of the working channel, the mounting tube is rotated and advanced to screw the spiral wire through the tissue surrounding the urethra where it is released from the holder and lodged in the prostate around the urethra. Optionally, a stylet (e.g., part of the delivery system or a separate rod, and in some embodiments, a balloon) is present in the urethra, to control the positioning of the wire relative to the urethral wall. Optionally or alternatively, the wire is inserted backwards, with the exposed tip of the wire being proximal to the far end of the delivery system which system may be inserted deeper into the body than the prostate. In an alternative embodiment, the wire is bent in an opposite helix to its natural shape, so that while it is fed forward, once the wire exits the delivery tube it screws proximally, rather than distally At 30, the mounting tube is screwed back (or pulled back) into the working channel, and then removed. Then, at 32, the working channel is removed from the urethra.

Optionally, a stent, for example, a temporary stent, is implanted in the urethra, for example, until it heals and/or the wire sets in place. Optionally or alternatively, a catheter for urinary drainage is implanted.

With reference now to FIGS. 3A-3C, a dilation wire 60 shown in the form of an elongated spiral, with two alternative exemplary cross-sections shown at FIG. 3B and FIG. 3C. Optionally, wire 60 has a circular cross-section, as indicated at 61a in FIG. 3B, or has a flattened cross-section as indicated at 61b in FIG. 3C. Optionally, the sides 61c of a flattened cross-section are rounded or otherwise shaped (e.g., thickened) to prevent damage to the surrounding urethral and prostate tissue during delivery and/or implantation. Optionally, the shape of the wire has a non-constant cross-section, for example, thereby defining joints at which the wire tends to bend. Optionally or alternatively, the cross-section is more complex than shown, for example, being undulating in a trans-axial direction, optionally with a constant thickness.

Optionally, the distal tip of the wire (not shown) may be enlarged and/or rounded for the same purpose. However, in some embodiments, such tip should be sufficiently sharp to pierce the tissue surrounded the urethra during implantation. In other embodiments, a separate sharp tip is provided by a delivery system, for example, as a holding tube.

The length of spiral wire 60 is determined by the longitudinal extent to which the urethra is to be dilated in a particular area. Such longitudinal extent may be, for example, less than 1 cm long, between 1 and 2 cm long, between 2 and 3 cm long or more, as required. Optionally, more than one spiral may be implanted along the urethra.

In an exemplary embodiment of the invention, the wire has a surface coverage (compared to a solid cylinder of same dimensions) of less than 10%, between 10% and 40%, between 40% and 80%, or smaller or intermediate or larger coverages. Optionally, the coverage is selected, for example, according to prostate tissue being able to squeeze between adjacent helix turns and cause stenosis and/or according to maintaining a desired blood flow and/or reducing foreign material in the body. In an exemplary embodiment of the invention, the helix has a pitch of, for example, 2, 4, 6, 10 or smaller, intermediate or large numbers of turns per cm length. In some cases, helixes with as few as 1, 2 or 3 turns may be used.

In an exemplary embodiment of the invention, the diameter of such a cylinder is, for example, 1 mm, 2 mm, 3 mm, 4 mm, 5 mm or smaller, intermediate or larger diameters (e.g., inner diameters or outer diameters). The diameter is optionally selected to account for expected further growth of the prostate.

In an exemplary embodiment of the invention, after implantation, flow in the prostate is substantially unobstructed, for example, having a lumen of at least 1 mm, 2 mm or 3 mm in diameter over at least 60%, 70%, 80% or 90% of the prostate when urine is ejected form the bladder. Optionally, such implantation allows normal emptying of the bladder, or at least emptying of at least 60%, 70%, 80% or other percentages of the bladder.

The diameter 61*a* (FIG. 3B) is optionally in the range of 0.2-3 mm. The flattened width 61*b* (FIG. 3C) is optionally in the range of 0.1-4 mm. The thickness 61*d* (FIG. 3C) is optionally in the range of 0.01-2 mm In an exemplary embodiment of the invention, the implant is selected of materials and has material properties and dimensions suitable to resist deformation by the prostate of more than 30%, 20% or 10%.

In an exemplary embodiment of the invention, when implanted, the wire is implanted (e.g., selection wire helix diameter vs. urethra diameter) so that there is a clearance of, on the average, 0.5 mm, 1 mm, 2 mm, 3 mm, or smaller, intermediate or larger amounts between the wire and the urethra. Optionally, the minima and/or maxima clearance are less than a factor of 4, 2, or 1.5 of such clearance.

In an exemplary embodiment of the invention, the surface of the wire is smooth. Optionally, the surface is made of a material or coated with materials that prevent tissue adhesion. In other embodiments, at least part of the wire is selected to have a surface that encourages surface adhesion, optionally, by being roughened. Optionally, the wire includes one or more outer barbs. Optionally, during implantation, such barbs or roughening are coated with a biodissolving material, such as a sugar, to prevent interference with implantation. Optionally or alternatively, the wire is delivered using a delivery tube which is pulled back after the wire is in place. Optionally, the tip and/or other parts of the wire include anchoring elements, optionally, as long as 1 mm or longer, which extend away form the wire. Optionally or alternatively, such anchoring elements are soft filaments, rather than rigid barbs.

While the wire has been generally described as being uniform, it may vary in shape, cross-section and/or material properties along its length. Optionally, the delivered wire has a uniform diameter. Alternatively, the diameter is non-uniform, for example, being designed to flare towards a bladder neck or being designed to be smaller where the prostate is less compressive. Optionally or alternatively, the diameter is greater in the middle of the prostate.

Wire 60 is made of a biocompatible material, for example, nitinol, stainless steel, or chromium-cobalt. Optionally, the surface of the wire may be coated or impregnated with a drug (e.g. sirolimus or paclitaxel) which is eluted over time, for example for between 1-7 days, 1-5 weeks or 1-4 months. Optionally, the drug is selected to prevent prostate growth and/or otherwise treat the prostate. Optionally or alternatively, the drug is selected to enhance or prevent fibrosis. Optionally or alternatively, the drug is selected to prevent inflammation and/or infection. Optionally, wire can 60 also be made of a biodegradable material, for example, suitable plastics, such as a polylactate. In some cases, the implantation will cause fibrosis which will support the prostate without the need for foreign device. In some embodiments, the wire is inserted for treatment of the prostate and may be inserted in a manner which does not encircle the prostate.

Optionally, wire 60 is formed of or coated with a radioactive material (e.g., beta, alpha or gamma emitting material). Optionally, such material can serve to treat the prostate and/or prevent restenosis. Optionally, it may be formed of a material or have a structure (e.g., coils) which can be heated by RF energy, for example, microwaves. Such heating may be used, for example, for prostate shrinking and/or to assist in removal of the wire.

Optionally, wire 60 can have elastic, super elastic or shape-memory properties that enable it to expand during and after implantation to provide further dilatation of the urethra. Optionally or alternatively, the wire is plastically deformable and is deformed by expanding a balloon in the urethra. Optionally, if restenosis occurs, further inflation is provided.

In some embodiments of the invention, the wire is a simple device optionally formed of a single material and which is passive or mechanically reactive to pressures applied thereto.

Figure 3D:
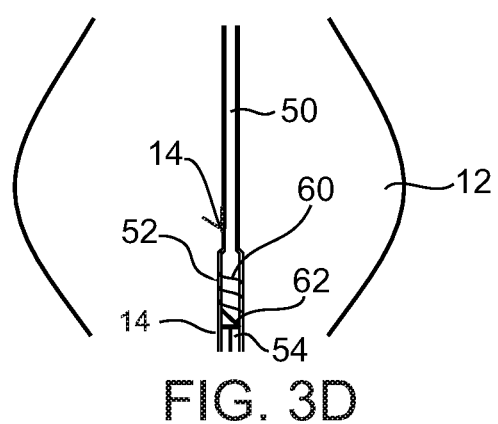
FIGS. 3D-3F illustrate an implantation device suitable for use with the device of FIGS. 3A-3C and progression of a method of implantation according to some embodiments of the invention, based, for example, on the method of FIG. 1.
Figure 3E:
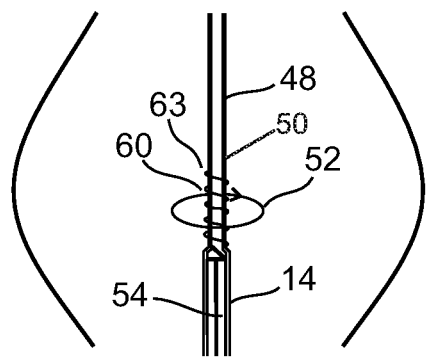
Figure 3F:
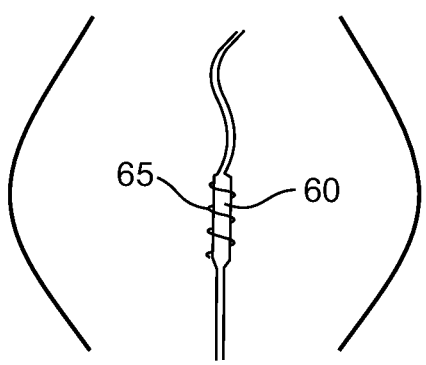

FIGS. 3D-3F show a delivery device 48 according to some embodiments of the invention. Delivery device 48 includes a mounting tube 50 and a holder 52. Spiral wire 60 is positioned at the proximal end of mounting tube 50 (i.e., toward the physician) for delivery, and attached at its proximal end to the distal end of holder 52. A slot 62 or other opening in holder 52 releasably receives the spiral wire. Holder 52 and mounting tube 50 with wire installed is optionally dimensioned to be slidable and rotatable in working channel 14 to facilitate delivery and implantation.

FIG. 3D shows wire 60 and delivery device 48 still within working channel 14. FIG. 3E shows some features of the method of installation. In FIG. 3E, holder 52 has been pushed through working channel 14 using handle 54 to the point where it is outside the working channel at a desired location for implantation. Here, handle 54 is rotated and advanced so the distal end 63 of wire 60 passes though the layer of tissue surrounding the urethra and is screwed into the prostate outside the urethra. Wire 60 is released from slot 62 once it has been screwed into the prostate, and holder 52 is unscrewed (or pulled back) and withdrawn into the working channel using handle 54. Delivery device 48 may then be withdrawn from the working channel and the working channel withdrawn from the urethra. Optionally, delivery device 48 may remain in the working channel while the latter is withdrawn.

While not shown, the delivery tube may be expandable, e.g., with the wire mounted on the outside of a balloon or the outside of a tube mounted on a balloon, or a self expanding tube.

FIG. 3F shows spiral wire 60 after implantation, according to some embodiments of the invention. Optionally, by providing a clearance around the urethra at 65, the urethra is allowed to decompress to provide the desired dilation. Optionally, by effectively providing a shield around the urethra, the wire prevents further enlargement of the prostate from causing recompression of the urethra.

Figure 4:
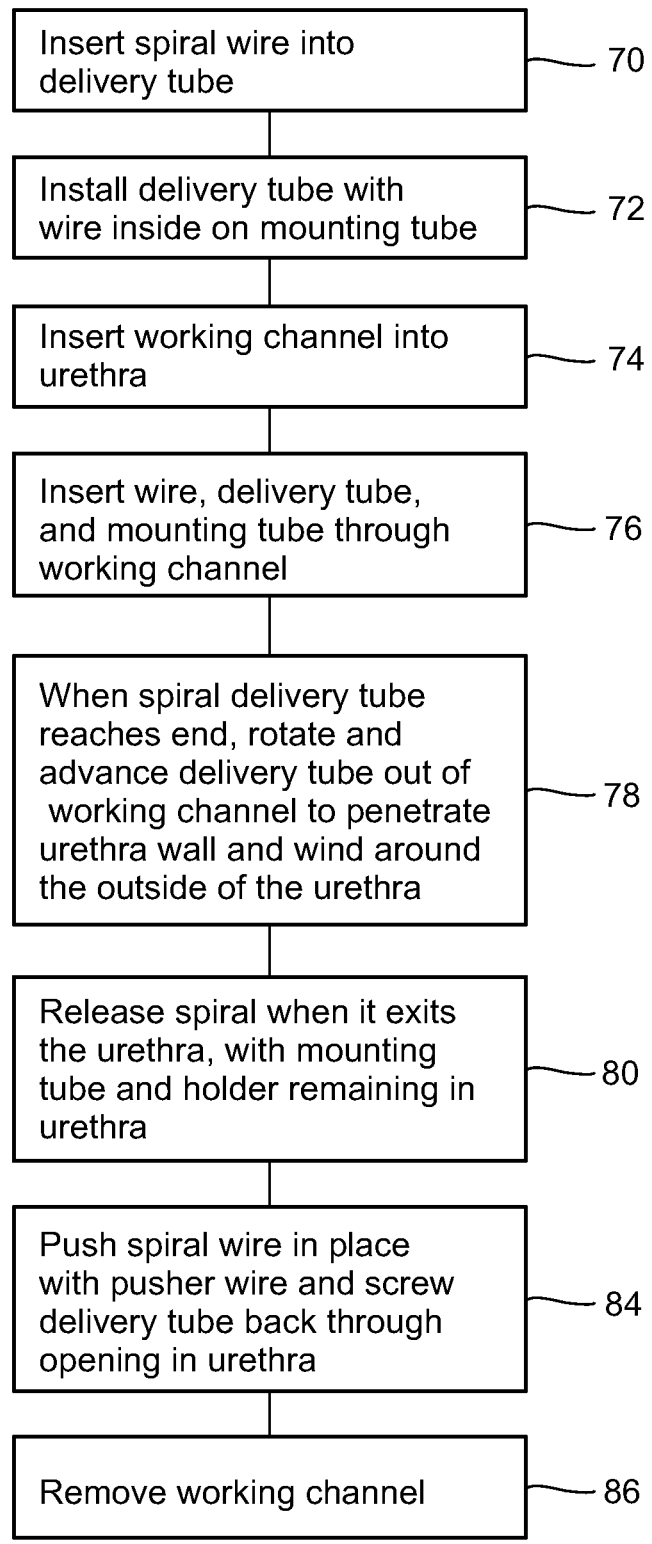
FIG. 4 is a flow diagram illustrating a urethral treatment method according to some other embodiments of the invention, as for example, the device of FIG. 3A.
Figure 5A:
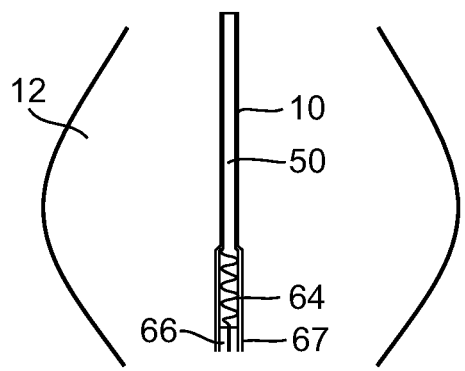
FIG. 5A-5E are a schematic illustration of a variation of the implantation device of FIGS. 3D-3F and progression of a method of implantation according to some embodiments of the invention, as for example, the method of FIG. 4.
Figure 5B:
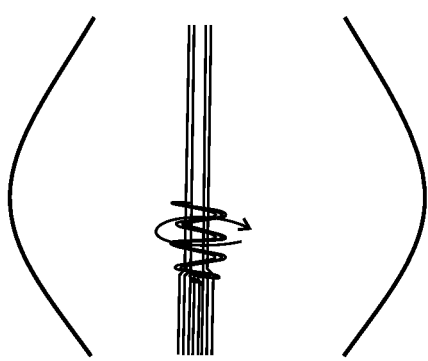

FIGS. 5A-5E, in conjunction with FIG. 4 illustrate a delivery device according to some embodiments, and a method of implantation. As shown in FIG. 5A, wire 60, which may be the same as that previously described, is contained in a closely fitting delivery tube or sheath 64. This may allow, for example, for the wire to be too soft for screwing into the tissue and/or having a surface not suitable for sliding past tissue as it is advanced. Optionally or alternatively, this allows for the wire to change its configuration after insertion, for example, to expand radially. For delivery, it is placed on a mounting tube 50. A pusher wire 66 extends through a passage 67 in mounting tube 50. In some embodiments of the invention, use of sheath 64 facilitates using a wire with a known configuration and enables insertion of a wire with shape-memory to further expand post delivery once sheath 64 is removed. The construction may otherwise be as previously described. Optionally, sheath 64 is formed of any biocompatible metal, and may be provided with a low friction coating, for example, as explained below.

Referring to FIG. 4, a method of implantation of the embodiment of FIG. 5A is shown which is also generally similar to that previously described in connection with FIG. 1, with one or more of the following variations. At 70, the wire 60 inserted in delivery tube 64, and at 72, the wire (inside the delivery tube), is installed on mounting tube 50, and pusher wire 66 is inserted. At 74 and 76, the working channel 14 is inserted, and the wire 60, delivery tube 64, and wire 66 are pushed through the working channel until the distal part of the delivery tube reaches the end of the working channel. Then, at 78, the delivery tube and the mounting tube are rotated and advanced to screw the delivery tube with the wire still inside to the prostate around the urethra (see FIG. 5B).

Figure 5C:
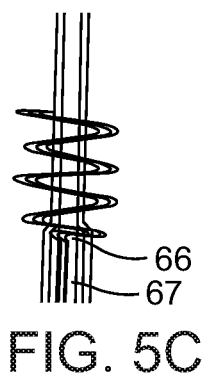
Figure 5D:
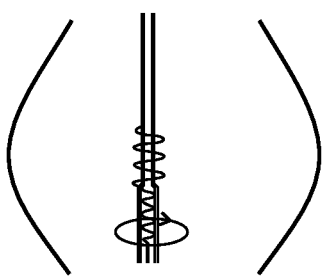

At 80, wire 60 is pushed out of the delivery tube 64 by pusher wire 66 until the wire itself is implanted around the urethra FIG. 5C). Then, at 84, delivery tube 64 is screwed back (or, for example, if soft, pulled back) into the working channel while the pusher wire 66 holds wire 60 in place (FIG. 5D). A suitable handle or lock (not shown) may be provided on mounting tube 50 for this purpose. Optionally or alternatively, the tip of the wire anchors (e.g., by including a barb) and then delivery tube 64 can be pulled back without retracting the wire. At 86, the working channel is removed.

Figure 5E:
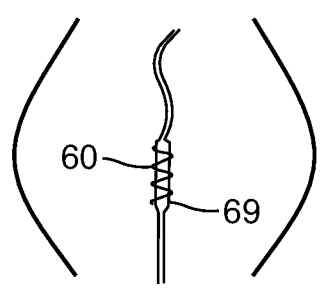

FIG. 5E shows spiral wire 60 implanted around the urethra and providing a clearance at 69 to prevent recompression of the urethra.

Figure 6:
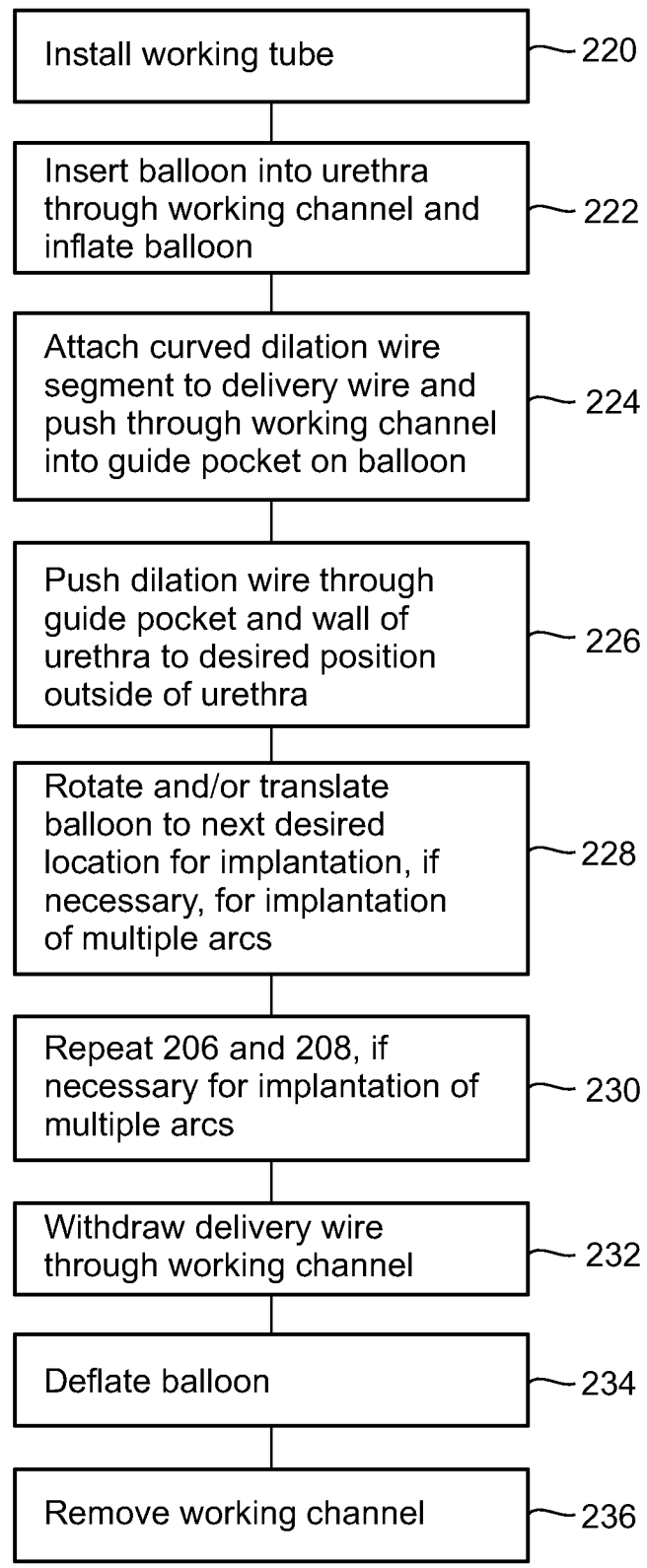
FIG. 6 is a flow diagram illustrating a urethral treatment method according to some embodiments of the invention.
Figure 8A:
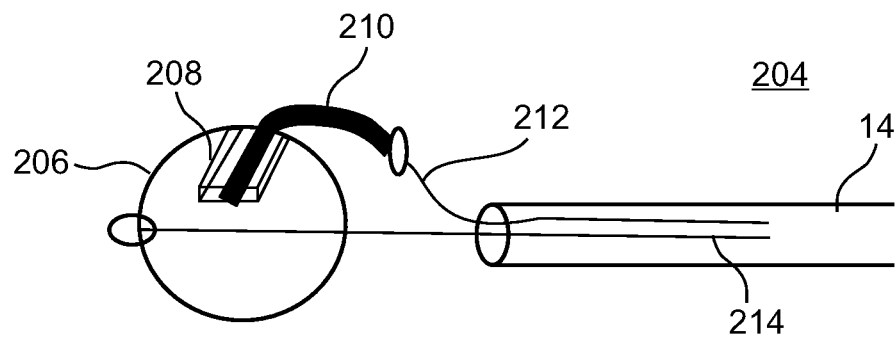
FIG. 8A shows, in schematic form, an implantation apparatus according to some embodiments of the invention by which separate curved wires can be implanted, for example, by the method of FIG. 6

FIG. 6 is a flow chart illustrating another delivery method suited for example, for implanting a wire formed of one or more discrete elements such as arcs (e.g., c-shaped wires) as illustrated in FIGS. 7C-7E, and a delivery device for the method of FIG. 6 as shown in FIG. 8A. As context for the method of FIG. 6, FIG. 7A shows in cross-section, prostate 200 and a urethral passage 202 the generally triangular shape of which has been compressed to the point of virtual blockage by enlargement of the prostate.

Referring to FIG. 8, delivery device 204 includes a balloon 206 optionally having a guide pocket 208 on its outer surface. A wire 210 in the form of a generally C-shaped arc is attached to a delivery wire 212. An inflation tube 214 is provided to inflate balloon 206. All of these are sized to pass through working channel 14 to a desired implantation site.

Separate curved sections 210 can be useful, for example, due to the variation of the structure in different patients, thereby enabling flexibility in the installation of support for the urethra. As in the case of the spiral wire, the curved sections may have round or flattened cross-sections optionally, with rounded sides.

Referring to FIG. 6, at 220, working channel 14 is installed. At 222, balloon 206 is inserted into the urethra through working channel 14 and the balloon is inflated through 214. This is shown in FIG. 7B, with all but corners 207 expanded to the contour of the expanded balloon. Corners 207 are not fully expanded to illustrate a situation where inflation is insufficient. In this condition there is some danger of restenosis and/or danger of the wire transfixing the urethra.

At 224, a curved dilation wire segment 210 (FIG. 7C) is attached to delivery wire 212 and pushed through working channel into guide pocket 208 on balloon 206 (FIG. 8A). Other wire segment shapes can be used as well, for example, substantially straight segments and segments with a curvature both for the circumference of the urethra and to support an axial orientation. Thus, for example, a wire segment may be selected to be a section of a circle or a section of a helix. Optionally, the segment is curved, but is not part of a circle. For example, the section may have a greater radius of curvature at one or both ends, than at a center thereof. In another embodiment, the curvature of the element is a monotonic (increasing or decreasing) function along its length.

At 226, dilation wire 210 is pushed into and through guide pocket 208 and the tissue around the urethra to desired position outside of the urethra (see FIG. 7C). Movement of delivery wire 212 may be controlled manually or in any other suitable way, for example, with a foot pedal. The process is controlled visually or by ultra sound, for example.

In an exemplary embodiment of the invention, the insertion (e.g., and/or directing of guide) is circumferential. Optionally or alternatively, the direction is at least in part axial. Optionally, the angle to the axis of the urethra is, for example, 90 (no axial component), 80, 70, 50, 30, or 10 degrees, or intermediate or smaller angles.

At 228, if more than one arc 210 is to be implanted as shown in FIG. 7D, balloon 206 is rotated and/or translated to a next desired location for implantation, and at 230, implantation through guide pocket 208 is repeated the necessary number of times.

Optionally, the segments are inserted to have some overlap, for example, 10%, 20%, 30%, 50%, 70% or smaller or intermediate amounts of overlap in a circumferential direction between two adjacent segments. Optionally or alternatively, such overlap is provided in an axial extent. In an exemplary embodiment of the invention, a surrounding of the urethra is provided by, for example, 1, 2, 3, 4 or 5 segments. Optionally, at least some of the urethra is not enclosed, for example, 20% or 30% by angle, for example, a bottom section. Optionally, a density of segments is different in different angular positions relative to urethra, for example, being different by a factor of, for example, 1.3, 2, 3 or intermediate factors.

Optionally, a complete dilation device comprises 3, 5, 6, 8, 10, 15 or smaller or intermediate or larger number of arc sections.

After insertion, diameter of the structural support and/or urethral diameters can be, for example as for a single helical wire. Optionally, the shape of the support can deviate form that of a cylinder, for example, as shown in FIG. 7E, the shape of a polygon with 3, 4, 5 or other numbers of sides.

At 232, delivery wire 212 is withdrawn through working channel 14. At 234, balloon 206 is deflated and withdrawn into working channel 14. At 236 working channel 14 is withdrawn. Optionally delivery wire 212 and balloon 206 are retained in the working channel while it is withdrawn.

FIG. 7E shows multiple arcs in place providing clearance to restore urethral passage 238 to a dilated or semi-dilated condition. As previously described, arcs 240 can prevent recompression of the urethra due to continued expansion of the prostate.

Figure 8B:
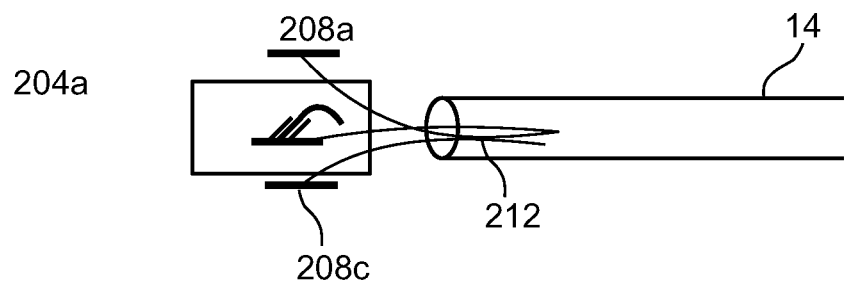
FIG. 8B shows a variation of the implantation apparatus of FIG. 8A, according to some embodiments of the invention.

An alternative delivery device 204a for a C-shaped wire is shown in FIG. 8B. This differs from the embodiment of FIG. 8A in that multiple (e.g., 2, 3, 4, 5 or more) guide pockets 208a-208c are provided on balloon 206, e.g., at multiple circumferential and/or axial positions. Each guide pocket is preloaded with each arc segment, optionally attached to its own delivery wire 212 before insertion through working channel 14. Alternatively, a single pusher is used for all wires. Movement of delivery wires 212 may be controlled manually or in any other suitable way, for example, with a foot pedal. The process is optionally controlled visually or by ultrasound, for example.

Implantation device 204a can avoid the need to rotate balloon 206 for circumferential implantation of multiple arcs.

Figure 9:
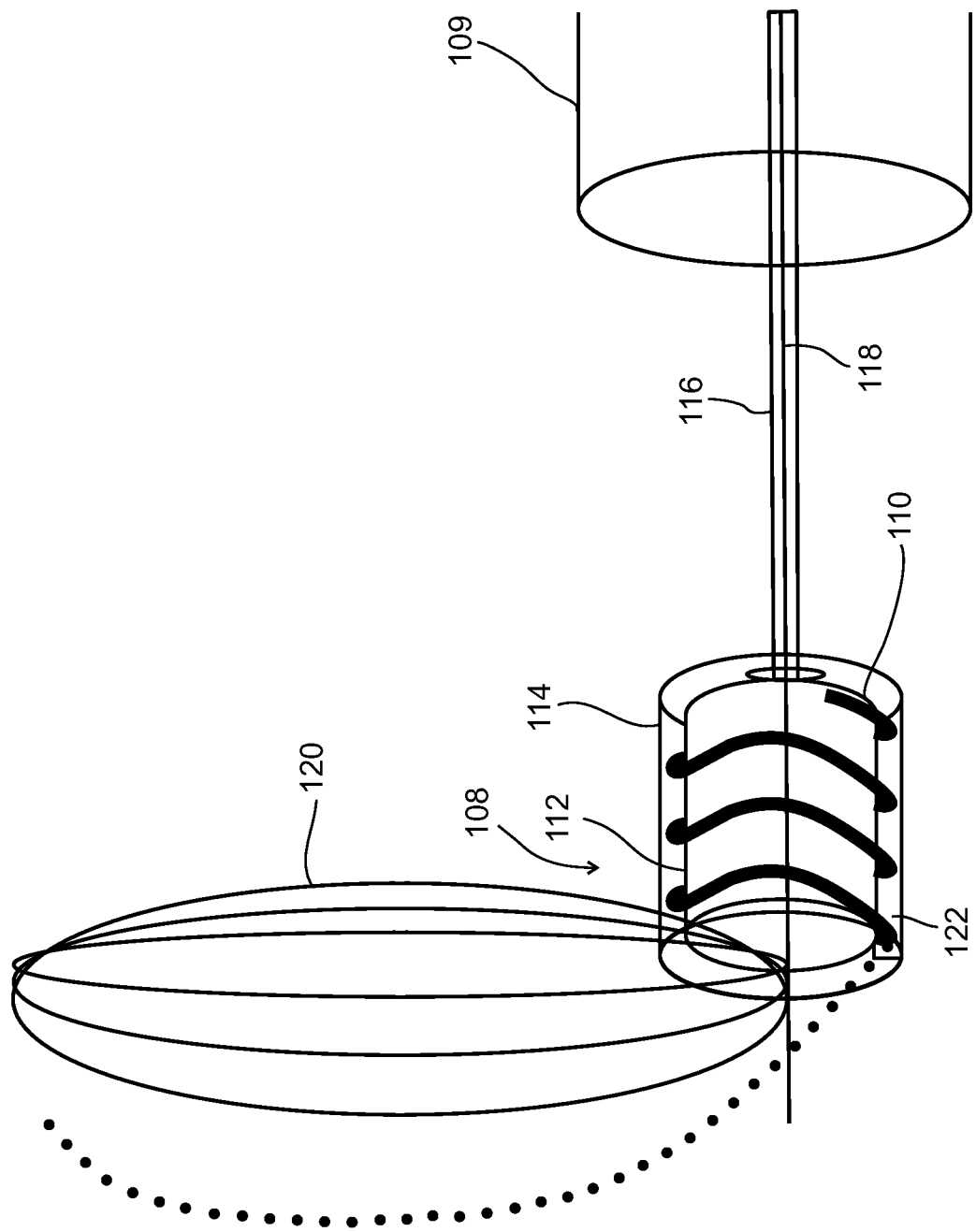
FIG. 9 illustrates in schematic form an implantation apparatus according to some embodiments of the invention which may be used to practice the method, for example, of FIG. 10, for implanting spiral wires or separate curved sections.
Figure 10:
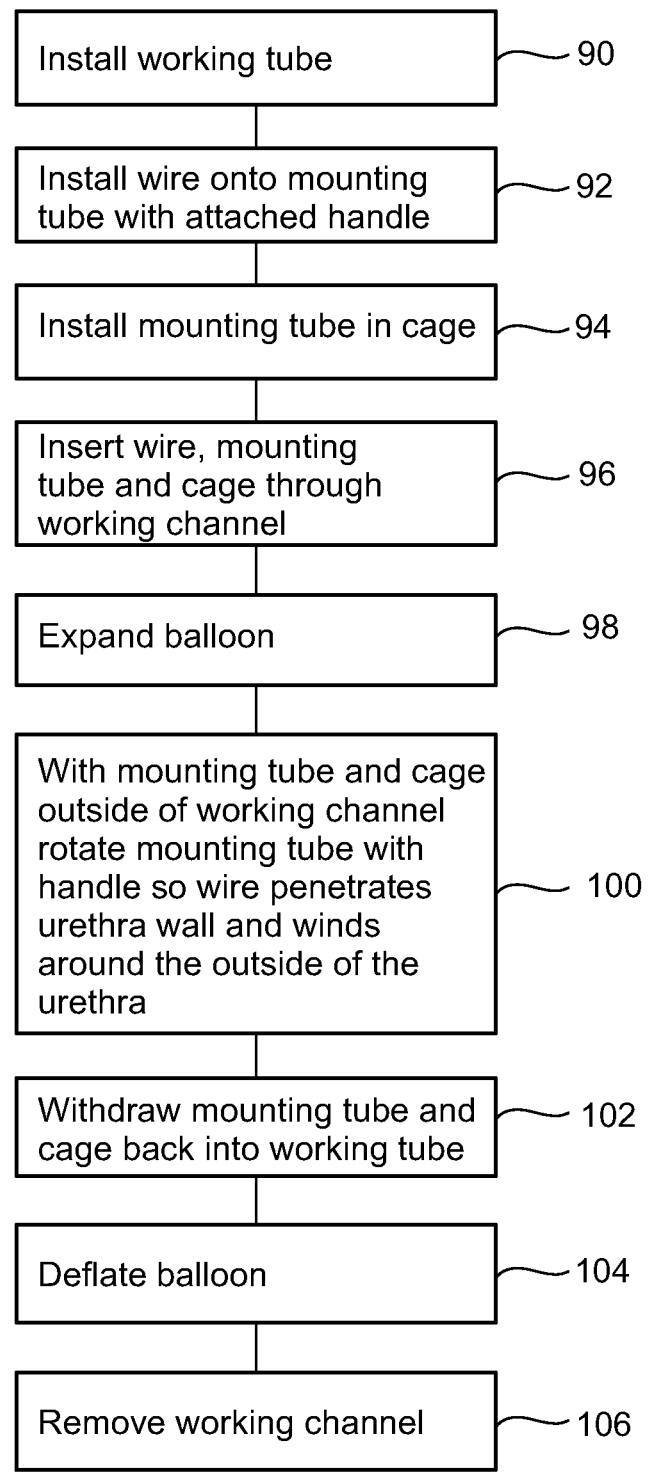
FIG. 10 is a flow diagram illustrating a urethral treatment method utilizing the apparatus of FIG. 9, according to some embodiments of the invention.

FIG. 10 shows a delivery method according to some embodiments using a delivery device 108 illustrated in FIG. 9. The method of FIG. 10 and delivery device 108 can be used for implantation of dilation devices in the form of a spiral or of multiple C-shaped sections. This installation method employs an inflatable balloon, but instead of being located radially, it is positioned at one side of the urethra and expands diametrically. This has the potential benefit of having the mounting tube at the urethra wall, therefore enabling screwing the device in a rotational movement, almost perpendicular to the insertion direction. Optionally or alternatively, a benefit of using a plain balloon is provided, as the guiding mechanism may be provided on a separate element.

Referring to FIG. 9, delivery device 108 is comprised of a mounting tube 112, an attached handle 116 and a cage 114. Tube 112, carrying a wire (e.g., segments or a complete helix) 110, shown, for example, as a spiral (noting that even a segment may be delivered as a spiral), is positioned in cage 114 and delivered to an implantation site through a working channel 109. Cage 114 prevents device 110 from opening inside the working channel. An opening 122 at the distal end of cage 114 is provided to allow wire 110 to exit for implantation.

A balloon 120, for example, carried by a hollow expansion tube 118 passing through holder 116 is positioned at the distal end of mounting tube 112. Optionally balloon 120 may be attached to mounting 112, for the purpose of fixed location of the balloon relatively to the opening 122 at the distal end of cage 114. Alternatively, the balloon is provided on a separate element, optionally allowing relative movement and/or rotation.

As shown, balloon 120 has a relatively short axial extension. Alternatively, a greater axial extension, for example, of 5 mm, 10 mm, 20 mm or other amount, is provided.

Referring now to FIG. 10, at 90, working channel 109 is inserted in a urethra to be treated. At 92, dilation wire 110 is installed on mounting tube 112, and inserted into cage 114. At 96, cage 114 is inserted through working channel 109.

At 98, balloon 120 is expanded. As shown, cage 114 is positioned at one side of the urethra, and balloon 120 is configured to expand diametrically. This can be advantageous to allow direct insertion of the wire by a rotational movement at the desired direction. At 100, holder 116 is rotated and advanced out of working channel 109 allowing wire 110 to exit though an open area 122 as mounting tube 112 is rotated. Optionally, rotation of mounting tube 112 allows wire 110 to pass through the urethra wall, and become implanted in the surrounding area of the prostate. Optionally or alternatively, a pusher wire (not shown) is used to push wire 110. In an alternative embodiment, tube 112 is rotated, rotating wire 110 with it, while cage 114 is not rotated. Balloon 120 is optionally fixed in position relative to mounting tube 112.

At 102, the implantation device 108 is withdrawn back into working channel 109. At 104, balloon 120 is deflated, and delivery device is withdrawn through working channel 109 At 106, the working channel is withdrawn. Delivery device 108 may optionally be retained in working channel 109 while it is being withdrawn.

In an exemplary embodiment of the invention, balloon 120 is expanded at a location with a known and/or fixed location relative to area 122. Optionally, balloon 120 does not rotate, however, this may be allowed in some embodiments of the invention.

In an exemplary embodiment of the invention, a delivery system and/or one or more wires and/or wire sections are provided as a kit, optionally with an indication for use (e.g., and/or printed instructions) in supporting a urethra and/or other particular organs. Optionally, such a kit includes a balloon. Optionally or alternatively, such a kit includes a cystoscope. Optionally or alternatively, such a kit includes the wire or sections mounted on the delivery system.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as limiting. In addition, any priority document(s) of this application is/are hereby incorporated herein by reference in its/their entirety.

What is claimed is:

1. A method for dilating a urethra using a dilation device and a delivery system comprising a balloon, the method comprising:
    a. loading said dilation device in a helix configuration on said delivery system;
    b. inserting said delivery system into said urethra;
    c. expanding said balloon thereby expanding said urethra and radially expanding said dilation device from said helix configuration to a C-shape arc configuration;
    d. implanting said dilation device in C-shape in a tissue of said urethra from outside the balloon, within an area of the urethra around the balloon, while the area of the urethra is expanded by the balloon.

2. The method of claim 1, wherein the dilation device is installed transurethrally.

3. The method of claim 1, wherein the dilation device is implanted by being pushed into the tissue of the prostate.

4. The method of claim 1, wherein the dilation device is implanted by being advanced into the tissue of the prostate using an overtube.

5. The method of claim 1, further comprising expanding or allowing the expansion of the dilation device post-implantation.

6. The method of claim 1, wherein the dilation device is in the form of one or more separate arcuate-shaped sections.

7. The method of claim 1, wherein the dilation device is formed of a material which expands outwardly around the urethra during and/or after implantation.

8. The method of claim 1, comprising shaping the urethra using the balloon prior to or during said implanting.

9. The method of claim 8, comprising not rotating said balloon during said implanting.

10. The method of claim 1, comprising selecting said dilation device length and position to not interfere with an inner bladder valve.

11. The method of claim 1, wherein said dilation device provides clearance between the enlarged prostate and a lumen of the urethra, and prevents recompression of the urethra due to further enlargement of the prostate.

12. The method according to claim 1, wherein the dilation device has a substantially flat cross-section.

13. The method according to claim 1, wherein upon implantation, no more than or about 30% by angle of the constricted portion of the urethra is not surrounded.

14. The method according to claim 13, wherein the portion of the urethra that is not surrounded is at the bottom of the urethra.

15. The method according to claim 1, further including delivering the dilation device through the urethra for implantation in a compressed transverse-dimension configuration and expanding it for implantation.

16. The method according to claim 15, wherein the dilation device is formed of a plastically deformable material and is expanded by inflation of the balloon comprised in a delivery device.

17. The method according to claim 15, wherein the dilation device is formed of an elastically deformable material and is expanded by release from a mounting device comprised in a delivery device.

* * * * *